United States Patent
Ahmed et al.

(10) Patent No.: US 12,213,481 B1
(45) Date of Patent: Feb. 4, 2025

(54) **4,4'-[(2-HYDROXYPROPANE-1,3-DIYL) BIS(OXY)]DIBENZALDEHYDE AS AN ECO-FRIENDLY INSECTICIDAL AGENT AGAINST *SPODOPTERA LITTORALIS* (BOISD.)**

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Mohamed Gouda, Al-Ahsa (SA); Antar Ahmed Abdelhamid Ahmed, Al-Baha (SA); Mohamed A. Gad, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/655,571

(22) Filed: May 6, 2024

Related U.S. Application Data

(62) Division of application No. 18/400,079, filed on Dec. 29, 2023.

(51) Int. Cl.
| | | |
|---|---|---|
| *A01N 35/04* | (2006.01) | |
| *A01P 7/04* | (2006.01) | |
| *A01P 17/00* | (2006.01) | |
| *C07C 47/575* | (2006.01) | |

(52) U.S. Cl.
CPC ............... *A01N 35/04* (2013.01); *A01P 7/04* (2021.08); *A01P 17/00* (2021.08); *C07C 47/575* (2013.01); *C07C 2601/16* (2017.05)

(58) Field of Classification Search
CPC ............ A01N 35/04; A01P 7/04; A01P 17/00
See application file for complete search history.

(56) References Cited

PUBLICATIONS

Alakbar E. Huseynzada, Christian Jelch, Haji Vahid N. Akhundzada, Sarra Soudani, Cherif Ben Nasr, Aygun Israyilova, Filippo Doria, Ulviyya A. Hasanova, Rana F. Khankishiyeva, and Mauro Freccero, Synthesis, crystal structure and antibacterial studies of dihydropyrimidines and their regioselectively oxidized products doi: 10.1039/dora10255e.

Qamar Ali, Muhammad Raza Shah, Seik Weng Ng 4,4'-(Propane-1,3-diyldioxy)dibenzaldehyde DOI:10.1107/S1600536810021124.

Davie Cappoen, Delphine Forge, Frank Vercammen, Vanessa Mathys, Mehdi Kiass, Virginie Roupie, Roel Anthonissen, Luc Verschaeve, Jean Jacques Vanden Eynde, and Kris Huygen Biological evaluation of bisbenzaldehydes against four *Mycobacterium* species DOI:10.1016/j.ejmech.2013.03.023.

A. Guerrero, Edi A. Malo, J. Coll & C. Quero Semiochemical and natural product-based approaches to control *Spodoptera* spp. (Lepidoptera: Noctuidae), DOI:10.1007/s10340-013-0533-7.

Antar A. Abdelhamid, M.M. Elwassimy, Safwat A. Aref, and Mohamed A. Gadb, Chemical design and bioefficacy screening of new insect growthregulators as potential insecticidal agents against Spodoptera littoralis (Boisd.) DOI:10.1016/j.btre.2019.e00394.

*Primary Examiner* — Snigdha Maewall
(74) *Attorney, Agent, or Firm* — Nath, Goldberg & Meyer; Joshua B. Goldberg

(57) ABSTRACT

Synthesis of a compound 4,4'-[(2-hydroxypropane-1,3-diyl) bis(oxy)]dibenzaldehyde and its use as an insecticidal agent.

12 Claims, 1 Drawing Sheet

4,4'-[(2-HYDROXYPROPANE-1,3-DIYL)BIS(OXY)]DIBENZALDEHYDE AS AN ECO-FRIENDLY INSECTICIDAL AGENT AGAINST *SPODOPTERA LITTORALIS* (BOISD.)

CROSS-REFERENCE TO RELATED APPLICATION

This application is a divisional of U.S. patent application Ser. No. 18/400,079, filed on Dec. 29, 2023, the entire contents of which are incorporated herein by reference.

BACKGROUND

1. Field

The present disclosure relates to synthesis of the compound 4,4'-[(2-hydroxypropane-1,3-diyl)bis(oxy)]dibenzaldehyde and its use as an insecticidal agent.

2. Description of the Related Art

According to the majority of problems brought on by the use of pesticides, the use of safe and distinctively tailored organic components is necessary for development in order to decrease the effects of pesticide compounds. Juvenile hormone analogues as an example of insect growth regulators may be promising due to their defined mechanism of action on pests and lower poisonousness towards vertebrates than traditional insecticides. As a result, a special collection of pure insect growth regulators has been created.

Insect growth regulators (IGRs) are third-generation insecticides less toxic and compatible with insect pest management that were developed to reduce the pollution of food and environment. These compounds have a specific mode of action on insects and a lower toxicity against vertebrates than conventional insecticides for this purpose, the endocrine system of insects has been intentionally targeted for insecticidal activity. The developed insecticides are used to suppress insect populations, stopping their proliferation by disrupting their normal endocrine functions. Juvenile hormone mimics (e.g., methoprene (1), fenoxycarb (2)), anti-juvenile hormones (e.g., precocene II), and ecdysone analogs (e.g., tebufenozide (3)) are some examples illustrated below:

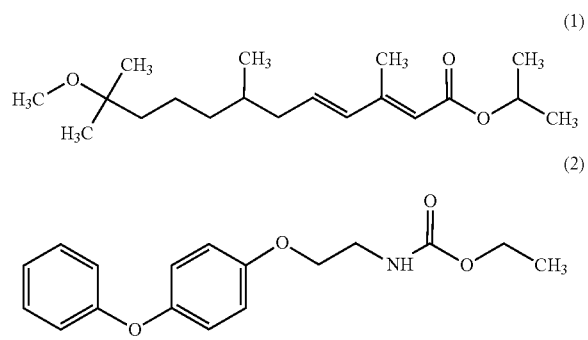

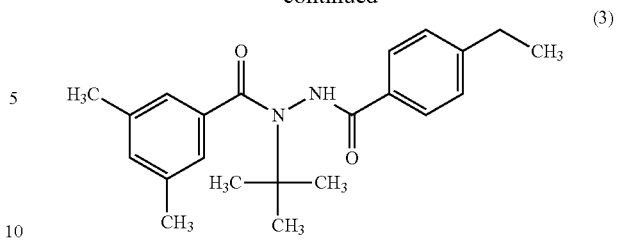

Other IGR compounds such as teflubenzuron and hexaflumuron act preferentially by interfering with the chitin synthesis metabolism (chitin synthesis inhibitors). These substances appear to have a high target pest specificity and their effects can differ significantly among insect species. Some IGRs are considered highly toxic ($LC_{50}$ 100-1000 mg/L for tebufenozide) to very highly toxic ($LC_{50}$<100 mg/L for fenoxycarb and methoprene) for aquatic insects. Endocrine-disrupting compounds (EDCs) is a term commonly used to describe these substances that potentially interfere with hormones. Until now, observations on the impact of EDCs mainly focused on vertebrates and steroid substances. Endocrine disruption has also been relatively well studied in aquatic invertebrates but hardly any information is available on soil invertebrates. Studies on the toxicity of IGRs are mainly conducted by chemical companies producing or marketing the product or with their financial support and focused principally on target pest organisms.

From an environmental and economic perspective, it is becoming clear that the traditional methods of proceeding chemical synthesis are unsustainable and have to be changed. Microwave (MW) produces a powerful way to do synthetic chemistry in the light of the current paradigm shift to "green chemistry." Not only can it reduce chemical reaction times from hours to minutes but it can also reduce side reactions, increase yields, and enhance reproducibility compared with conventional heating conditions. According to the current synthetic requirements, environmentally benign procedures for synthesis new organic compounds employing MW methodology are particularly welcome.

Thus, new insecticides and/or pesticides solving the aforementioned problems using green chemistry methods are desired.

SUMMARY

The present subject matter relates to the synthesis of a unique pure insect growth regulator, as well as the regulator itself. The structure of this synthesized compound, which is related to the most well-known insect growth regulator insecticides, can be confirmed by elemental and contemporary spectroscopic investigations (IR, UV, $^1$HNMR, $^{13}$CNMR, and elemental analysis). The target compound 4,4'-[(2-hydroxypropane-1,3-diyl)bis(oxy)]dibenzaldehyde 1 can be synthesized by the reaction of epichlorohydrin with 4-hydroxy benzaldehyde and a sodium hydroxide solution in high yields. The insecticidal efficacy of the chemically newly synthesized compound was checked against *Spodoptera littoralis* under laboratory conditions and compared with Fenoxycarb as a reference insecticide. It has been found that the present compound has a $LC_{50}$=25.62 mg/L, whereas Fenoxycarb has a $LC_{50}$=5.943 mg/L, indicating the insecticidal effectiveness of the present compound.

In an embodiment, the present subject matter relates to compositions containing, processes for making, and methods of using a 4,4'-[(2-hydroxypropane-1,3-diyl)bis(oxy)]dibenzaldehyde compound having the formula I:

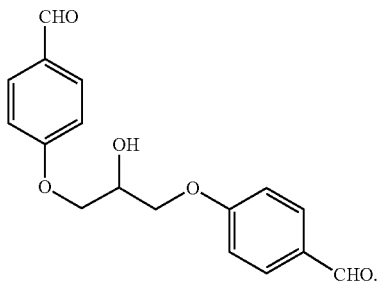

In another embodiment, the present subject matter relates to the use of an insecticidally acceptable composition comprising an insecticidally effective amount of the 4,4'-[(2-hydroxypropane-1,3-diyl)bis(oxy)]dibenzaldehyde compound and an insecticidally acceptable carrier.

In a further embodiment, the present subject matter relates to a method of killing insects comprising applying to said insects or to a target site of insect infestation an insecticidally effective amount of the 4,4'-[(2-hydroxypropane-1,3-diyl)bis(oxy)]dibenzaldehyde compound.

In an additional embodiment, the present subject matter relates to a method of repelling insects comprising applying to a target site of insect infestation an insect repelling effective amount of the 4,4'-[(2-hydroxypropane-1,3-diyl)bis(oxy)]dibenzaldehyde compound.

In one more embodiment, the present subject matter relates to a method of controlling an insect pest comprising applying to a target site of insect infestation an insect controlling effective amount of the 4,4'-[(2-hydroxypropane-1,3-diyl)bis(oxy)]dibenzaldehyde compound.

In a further embodiment, the present subject matter relates to a method of making the 4,4'-[(2-hydroxypropane-1,3-diyl)bis(oxy)]dibenzaldehyde compound, the method comprising: adding epichlorohydrin to 4-hydroxy benzaldehyde and sodium hydroxide to obtain a reaction mixture; stirring the reaction mixture to obtain a precipitate; filtering and recrystallizing the precipitate using an ethanol/dichloromethane mixture; and obtaining the 4,4'-[(2-hydroxypropane-1,3-diyl)bis(oxy)]dibenzaldehyde compound.

These and other features of the present subject matter will become readily apparent upon further review of the following specification.

DETAILED DESCRIPTION OF THE PREFERRED EMBODIMENTS

Figure 1A:
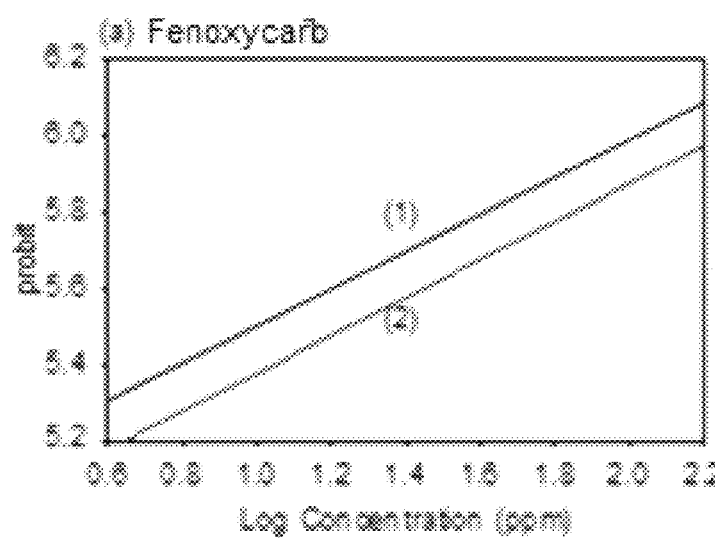
FIGS. 1A and 1B are charts showing insecticidal activity of the reference Fenoxycarb and the 4,4'-[(2-hydroxypropane-1,3-diyl)bis(oxy)]dibenzaldehyde compound (1), respectively, against S. littoralis after 72 hours of treatment.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of a unique pure insect growth regulator, as well as the regulator itself. The structure of this synthesized compound, which is related to the most well-known insect growth regulator insecticides, can be confirmed by elemental and contemporary spectroscopic investigations (IR, UV, $^1$HNMR, $^{13}$CNMR, and elemental analysis). The insecticidal efficacy of the chemically newly synthesized compound was checked against *Spodoptera littoralis* under laboratory conditions and compared with Fenoxycarb as a reference insecticide. It has been found that the present compound has a $LC_{50}$=25.62 mg/L, whereas Fenoxycarb has a $LC_{50}$=5.943 mg/L, indicating the insecticidal effectiveness of the present compound.

In an embodiment, the present subject matter relates to compositions containing, processes for making, and methods of using a 4,4'-[(2-hydroxypropane-1,3-diyl)bis(oxy)] dibenzaldehyde compound having the formula I:

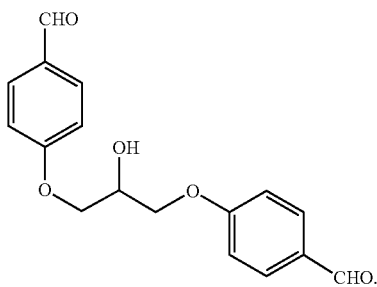

In certain embodiments, the 4,4'-[(2-hydroxypropane-1, 3-diyl)bis(oxy)]dibenzaldehyde compound can have a melting point of about 124° C. to about 126° C.

In additional embodiments, the 4,4'-[(2-hydroxypropane-1,3-diyl)bis(oxy)]dibenzaldehyde compound is considered as an insect growth regulator (IGR). Accordingly, the present compound is capable of inhibiting the life cycle of an insect.

In another embodiment, the present subject matter relates to an insecticidally acceptable composition comprising an insecticidally effective amount of the 4,4'-[(2-hydroxypropane-1,3-diyl)bis(oxy)]dibenzaldehyde compound and an insecticidally acceptable carrier.

In some embodiments, the present compositions and methods of use can be used for combination treatment, where other insecticidal ingredients can be included therein, or can be co-administered therewith.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art.

The present compounds are typically administered at an insecticidally effective dosage, e.g., a dosage sufficient to provide a desired activity against insects.

While insecticidal dosage levels have yet to be optimized for the present compounds, generally, each treatment of the present compositions could be expected to include from about 12.5 ppm to about 200 ppm, or mg/L, of the present compounds. In this regard, compositions having concentrations of the present compounds of about 200 ppm, about 100 ppm, about 50 ppm, about 25 ppm, or about 12.5 ppm, or mg/L, per application to a desired area of treatment are included within the present subject matter. The precise effective amount will vary from treatment to treatment and will depend upon the target area of application, the insect species being treated for, the number of insects present, and the like. The treatment area may be administered as many doses as is required to produce an effective treatment.

Liquid compositions can, for example, be prepared by dissolving, dispersing, etc. the active compound as defined above and optional adjuvants in a carrier, such as, for example, water, saline, aqueous dextrose, glycerol, glycols, ethanol, and the like, to thereby form a solution or suspension. If desired, the composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

In a further embodiment, the present subject matter relates to a method of killing insects comprising applying to said insects or to a target site of insect infestation an insecticidally effective amount of the 4,4'-[(2-hydroxypropane-1,3-diyl)bis(oxy)]dibenzaldehyde compound and/or a composition containing the same.

In an embodiment, the present methods of killing insects can be effective against insects belonging to a species *Spodoptera littoralis* (Boisd.). Further, the present compound can be considered as an insect growth regulator (IGR) that inhibits the life cycle of an insect, particularly *Spodoptera littoralis*. Accordingly, the present compound can be used as an insecticide to control populations of harmful insect pests, including, by way of non-limiting example, cockroaches and fleas.

Unlike classic insecticides, the present compound is unlikely to affect an insect's nervous system and is thus more friendly to "worker insects" within closed environments. The present compound can also be more compatible with pest management systems that use biological controls. In addition, while insects can become resistant to insecticides, they are less likely to become resistant to the present compound.

In another embodiment, in the present methods of killing insects, the 4,4'-[(2-hydroxypropane-1,3-diyl)bis(oxy)] dibenzaldehyde compound can have an $LC_{50}$ of about 25.62 mg/L against the species *Spodoptera littoralis* after 72 hours of treatment. In this regard, in the present methods of killing insects, the 4,4'-[(2-hydroxypropane-1,3-diyl)bis(oxy)] dibenzaldehyde compound can have an $LC_{50}$ of about 25.62 mg/L against $2^{nd}$ instars of larvae of the species *Spodoptera littoralis* after 72 hours of treatment.

Similarly, in the present methods of killing insects, the 4,4'-[(2-hydroxypropane-1,3-diyl)bis(oxy)]dibenzaldehyde compound can have an $LC_{50}$ of about 86.13 mg/L against the species *Spodoptera littoralis* after 72 hours of treatment. In this regard, in the present methods of killing insects, the 4,4'-[(2-hydroxypropane-1,3-diyl)bis(oxy)]dibenzaldehyde compound can have an $LC_{50}$ of about 86.13 mg/L or ppm against 4$^{th}$ instars of larvae of the species *Spodoptera littoralis* after 72 hours of treatment.

In a further embodiment of the present methods, the 4,4'-[(2-hydroxypropane-1,3-diyl)bis(oxy)]dibenzaldehyde compound can be applied to castor leaves.

In an additional embodiment of the present methods, about 12.5 to about 200 ppm of the 4,4'-[(2-hydroxypropane-1,3-diyl)bis(oxy)]dibenzaldehyde compound can be applied to the insects or to the target site. In this regard, about 200 ppm, about 100 ppm, about 50 ppm, about 25 ppm, or about 12.5 ppm, or mg/L, per application of the 4,4'-[(2-hydroxypropane-1,3-diyl)bis(oxy)]dibenzaldehyde compound can be applied to a desired area of treatment.

In an additional embodiment, the present subject matter relates to a method of repelling insects comprising applying to a target site of insect infestation an insect repelling effective amount of the 4,4'-[(2-hydroxypropane-1,3-diyl)bis(oxy)]dibenzaldehyde compound and/or a composition containing the same.

In an embodiment, the present methods of repelling insects can be effective against insects belonging to a species *Spodoptera littoralis* or *Spodoptera littoralis* (Boisd.).

In one more embodiment, the present subject matter relates to a method of controlling an insect pest comprising applying to a target site of insect infestation an insect controlling effective amount of the 4,4'-[(2-hydroxypropane-1,3-diyl)bis(oxy)]dibenzaldehyde compound.

In an embodiment, the present methods of controlling insect pests can be effective against insects belonging to a species *Spodoptera littoralis* or *Spodoptera littoralis* (Boisd.).

In a further embodiment, the present subject matter relates to a method of making the 4,4'-[(2-hydroxypropane-1,3-diyl)bis(oxy)]dibenzaldehyde compound, the method comprising: adding epichlorohydrin to 4-hydroxy benzaldehyde and a sodium hydroxide solution to obtain a reaction mixture; stirring the reaction mixture to obtain a precipitate; filtering and recrystallizing the precipitate using an ethanol/dichloromethane mixture; and obtaining the 4,4'-[(2-hydroxypropane-1,3-diyl)bis(oxy)]dibenzaldehyde compound.

The present production methods can be further seen by referring to the following Scheme 1:

Scheme 1

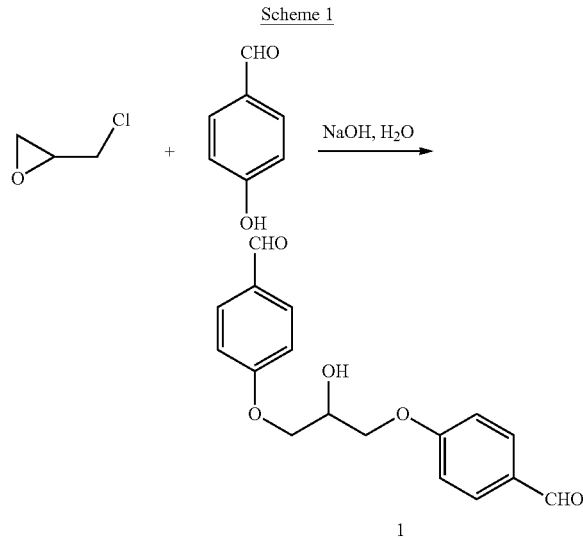

In an embodiment of the present production methods, the 4,4'-[(2-hydroxypropane-1,3-diyl)bis(oxy)]dibenzaldehyde compound can be obtained in an about 72% yield.

In certain embodiments, the reaction mixture may be stirred in an ice bath for at least about 4 hours.

In other embodiments of the present production methods, the 4,4'-[(2-hydroxypropane-1,3-diyl)bis(oxy)]dibenzaldehyde compound can be obtained as a white powder.

In further embodiments of the present production methods, the ethanol and dichloromethane in the ethanol/dichloromethane mixture can be in a 1:1 ratio.

The following examples relate to various methods of manufacturing certain specific compounds and application results as described herein. All compound numbers expressed herein are with reference to the synthetic pathway figures shown above.

EXAMPLES

Example 1

Preparation of 4,4'-[(2-hydroxypropane-1,3-diyl)bis(oxy)]dibenzaldehyde (2)

The reaction of epichlorohydrin (0.52 g) with 4-hydroxy benzaldehyde and a sodium hydroxide solution was stirred in an ice bath for 4 hours. The precipitating product was collected by filtration, washed thoroughly, and purified via crystallization from an ethanol/dichloromethane mixture (1:1).

Characterization Data of 4,4'-[(2-hydroxypropane-1,3-diyl)bis(oxy)]dibenzaldehyde (1)

White powder, yield: 72%; MP: 124-126° C. IR (ν) (KBr) cm$^{-1}$: 3482 (OH), 3072, (C—H$_{Aromatic}$), 2892 (C—H aliphatic), 1675 (C=O). $^1$HNMR (DMSO-d$_6$): δ 9.88 (s, 2H, 2CH), 7.01-7.88 (s, 8H Ar—H), 5.48 (s, 2H, 2OH), 4.2 (s, 5H, 2CH$_2$+CH), 3.8 (s, 6H, 2CH$_3$). Elemental analysis calculated for C$_{17}$H$_{16}$O$_5$(%) Calcd./found; C: 76.99/76.98, H: 5.37/5.35.

Example 2

Insecticidal Bioassay Screening

Five concentrations (200, 100, 50, 25, 12.5 ppm) were designed for this synthetic compound and the reference fenoxycarb's compound as the dynamic ingredients based on ppm via diluting the commercial formulation.

In this experiment, the synthetic compound was tested for its insecticidal bioactivity using the industry-standard leaf dip bioassay techniques. Preparation of the compound stocks to create 1000 ppm, 0.1 g of compounds 1-10 were dissolved in five mL of Dimethyl formamide & combined with 5 mL of distilled water. Until usage, the stocks were kept in a refrigerator. The target substance test results were noted & the concentrations needed to destroy 50% (LC$_{50}$) of *S. littoralis* larvae were calculated. The target compound was employed in five different concentrations, & 0.1% Tween 80 was employed as a surfactant. Castor bean leaf discs (nine centimeters in diameter) were dipped in the concentration under test for ten seconds, then fed to 2$^{th}$ & 4$^{th}$ larvae, which were roughly the same size and housed in glass jars (five pound). Each action carried out 3 times with ten larvae each. The mortality equalized via Abbott's formula. Calculations of mortality setback line were measurably rummage via probity analysis. Harmfulness index was strongminded via sun equations. The mortality results of larval insect were estimated through employing probit analysis through a statistics (LDP-line) equation which estimate the LC$_{50}$ values with 95% fiducially limits of lower, upper confidence limit and slope. The results of the bioassay screening can be observed in Table 1, below.

TABLE 1

Insecticidal bioeffecacy of second and fourth instars larvae of the laboratory strain of cotton leafworm, *S. littoralis* to test product (1) after 72 hours of treatment.

| Comps. | 2$^{nd}$ instar larvae | | | 4$^{th}$ instar larvae | | |
|---|---|---|---|---|---|---|
| | LC$_{50}$ (mg/L) at 95% | Slope | Toxicity index % | LC$_{50}$ (mg/L) at 95% | Slope | Toxicity index % |
| 1 | 25.62 | 0.246 ± 0.0792 | 22.93 | 86.13 | 0.297 ± 0.097 | 69.54 |
| fenoxycarb | 5.943 | 0.298 ± 0.0808 | 100 | 59.914 | 0.225 ± 0.0870 | 100 |

Notes:
$^a$Toxicity ratio is estimated as fenoxycarb's LC$_{50}$ value for baseline toxicity/the compounds' LC$_{50}$ value * 100.

Figure 1B:
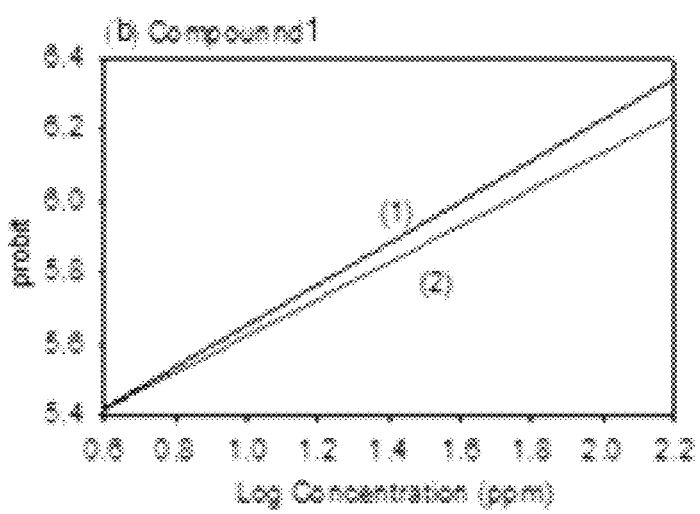

From this data, and as seen in FIGS. 1A-1B, it is observed that the present compound is active against *Spodoptera littoralis* as it is close in activity to the reference insecticide, Fenoxycarb. The 2nd instar larvae are represented by line (1) and 4th instar larvae are represented by line (2) in each graph.

It is to be understood that the methods of making and using the 4,4'-[(2-hydroxypropane-1,3-diyl)bis(oxy)]dibenzaldehyde (1) compound, and the use of compositions containing the same, are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of killing insects comprising applying to said insects or to a target site of insect infestation an insecticidally effective amount of an insecticidally active composition comprising an insecticidally effective amount of a 4,4'-[(2-hydroxypropane-1,3-diyl)bis(oxy)]dibenzaldehyde compound having the formula I:

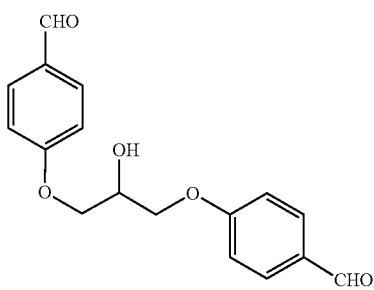

and an insecticidally acceptable carrier.

2. The method of killing insects of claim 1, wherein the insects belong to a species *Spodoptera littoralis*.

3. The method of killing insects of claim 2, wherein the 4,4'-[(2-hydroxypropane-1,3-diyl)bis(oxy)]dibenzaldehyde compound has an LC$_{50}$ of about 25.62 mg/L against the species *Spodoptera littoralis* after 72 hours of treatment.

4. The method of killing insects of claim 2, wherein 4,4'-[(2-hydroxypropane-1,3-diyl)bis(oxy)]dibenzaldehyde compound has an LC$_{50}$ of about 25.62 mg/L ppm against 2$^{nd}$ instars of larvae of the species *Spodoptera littoralis* after 72 hours of treatment.

5. The method of killing insects of claim 2, wherein the 4,4'-[(2-hydroxypropane-1,3-diyl)bis(oxy)]dibenzaldehyde compound has an LC$_{50}$ of about 86.13 mg/L against the species *Spodoptera littoralis* after 72 hours of treatment.

6. The method of killing insects of claim 2, wherein the 4,4'-[(2-hydroxypropane-1,3-diyl)bis(oxy)]dibenzaldehyde compound has an LC$_{50}$ of about 86.13 mg/L ppm against 4$^{th}$ instars of larvae of the species *Spodoptera littoralis* after 72 hours of treatment.

7. The method of killing insects of claim 1, wherein the 4,4'-[(2-hydroxypropane-1,3-diyl)bis(oxy)]dibenzaldehyde compound is applied to castor leaves.

8. The method of killing insects of claim 1, wherein about 12.5 to about 200 ppm of the 4,4'-[(2-hydroxypropane-1,3-diyl)bis(oxy)]dibenzaldehyde compound is applied to the insects or to the target site.

9. A method of repelling insects comprising applying to a target site of insect infestation an insect repelling effective amount of an insecticidally active composition comprising an insect repelling effective amount of a 4,4'-[(2-hydroxypropane-1,3-diyl)bis(oxy)]dibenzaldehyde compound having the formula I:

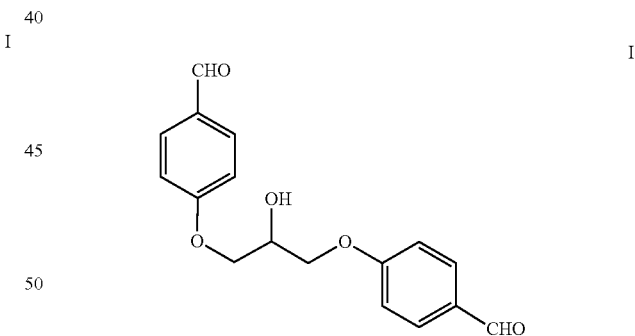

and an insecticidally acceptable carrier.

10. The method of repelling insects of claim 9, wherein the insects belong to a species *Spodoptera littoralis*.

11. The method of repelling insects of claim 9, further comprising controlling an insect pest comprising applying to a target site of insect infestation an insect controlling effective amount of the insecticidally active composition.

12. The method of claim 11, wherein the insect pest belongs to a species *Spodoptera littoralis*.

* * * * *